United States Patent [19]
Rudolph, Jr.

[11] Patent Number: 5,634,905
[45] Date of Patent: Jun. 3, 1997

[54] APPARATUS FOR THE PREVENTION OF RETROGRADE MOVEMENT OF FLUIDS DURING THE USE OF AIR ELIMINATING FILTERS IN INTRAVENOUS THERAPY

[75] Inventor: James E. Rudolph, Jr., New Castle, Del.

[73] Assignee: W. L. Gore & Associates, Inc., Newark, Del.

[21] Appl. No.: 599,881

[22] Filed: Feb. 14, 1996

[51] Int. Cl.⁶ .................................................. A61M 1/00
[52] U.S. Cl. ........................ 604/122; 604/120; 210/436; 210/472
[58] Field of Search .................................. 604/122, 126, 604/127; 210/120, 472, 436

[56] References Cited

U.S. PATENT DOCUMENTS

| | | | |
|---|---|---|---|
| 4,034,754 | 7/1977 | Virag | 604/122 |
| 4,096,064 | 6/1978 | du Fresne | 210/120 |
| 4,116,646 | 9/1978 | Edwards | 604/126 |
| 4,861,466 | 8/1989 | Leoncavallo | 210/120 |
| 5,019,141 | 5/1991 | Granville | 210/120 |
| 5,549,816 | 8/1996 | Harp | 210/120 |

*Primary Examiner*—Sam Rimell
*Assistant Examiner*—Luke Yeh
*Attorney, Agent, or Firm*—Victor M. Genco, Jr.

[57] ABSTRACT

An apparatus is provided for preventing the retrograde movement of a prescribed fluid away from a patient during use of an air eliminating filter in intravenous therapy. Such retrograde fluid movement is prevented by employing at least one vented valve assembly to prevent the displacement of air into a proximal chamber of an air eliminating filter.

2 Claims, 3 Drawing Sheets

APPARATUS FOR THE PREVENTION OF RETROGRADE MOVEMENT OF FLUIDS DURING THE USE OF AIR ELIMINATING FILTERS IN INTRAVENOUS THERAPY

FIELD OF THE INVENTION

This invention generally relates to the field of intravenous therapy. More particularly, the present invention relates to the prevention of retrograde movement of fluids during use of air eliminating filters in intravenous therapy.

BACKGROUND OF THE INVENTION

Presently, intravenous fluid therapy protocols suggest the use of an air eliminating filter (AEF) during the administration of fluids to a patient. Typically, an air eliminating filter includes a primary filtration media comprising a hydrophilic microporous membrane having pore sizes ranging from about 0.2 µm to about 20.0 µm, and a vent comprising a hydrophobic microporous membrane having pore sizes ranging from 0.02 µm to 0.45µm.

Ideally, during actual intravenous administration of prescribed fluids to a patient, an AEF should be located in a position wherein the AEF is disposed at a level equal to an infusion site of the patient. However, in actual practice, the AEF will often be located in a position that is higher than the infusion site. Prescribed fluid flow rates through an AEF can range from as little as 2 milliliters per hour to over 1 liter per hour. However, when low fluid flow rates are coupled with an AEF being located higher than the infusion site, an environment will be created which permits retrograde movement of prescribed fluids away from the patient.

When an AEF is located in a position that is higher than the infusion site of the patient, the AEF will develop a head pressure because the AEF is vented. This head pressure causes the free flow of fluids from the proximal chamber of the AEF, and therefore, causes the proximal chamber to empty. The proximal chamber will remain empty as long as the AEF is higher than the infusion site. This empty proximal chamber is the primary factor in contributing to the retrograde movement of prescribed fluids away from the patient.

Because most patients receiving intravenous therapy are either fully ambulatory, or are able to move about in their beds, the position of the AEF relative to the infusion site changes. Typically, such position changes result in the AEF going from a position higher than the infusion site, to a position that is lower than the infusion site. At this juncture, there is a negative pressure gradient formed between the patient and the AEF. Consequently, fluid in the intravenous tubing distal to the AEF, and body fluids from the patient, freely move in a retrograde manner up the intravenous tubing and away from the patient.

Retrograde movement of fluids can cause serious clinical situations to arise. More particularly, during retrograde movement of fluids, the patient does not receive prescribed intravenous fluids. Also, the retrograde movement of body fluids, in particular blood, can cause clots to form in the intravenous tubing distal to the AEF, or in the infusion catheter. If a clot is formed, costly procedures must be initiated to dissolve the clot, or the infusion must be discontinued. Such a discontinuation requires the removal of an infusion catheter, the location of a new infusion site, and the supply of a new AEF filter and support assembly. As may be appreciated, this results in higher medical costs and additional physical and mental trauma for the patient.

The foregoing illustrates limitations known to exist in present intravenous therapy techniques and assemblies. Thus, it is apparent that it would be advantageous to provide an improved apparatus and method directed to overcoming one or more of the limitations set forth above. Accordingly, a suitable alternative is provided including features more fully disclosed hereinafter.

SUMMARY OF THE INVENTION

The present invention advances the art of intravenous therapy beyond which is known to date. In one aspect of the present invention, an improved air eliminating filter is provided for use in intravenous therapy. The air eliminating filter has a proximal fluid chamber disposed in fluid communication with a proximal fluid inlet, and a distal fluid chamber disposed in fluid communication with a distal fluid outlet. The proximal fluid chamber and the distal fluid chamber are fluidly connected through a liquid filter element. The improvement comprises a vent including a one-way gas valve assembly which: 1) permits gases to vent from the proximal fluid chamber through the venting means to an external atmosphere; and 2) restricts a flow of gases from the external atmosphere through the venting means into the proximal fluid chamber.

Accordingly, it is a primary purpose of the present invention to prevent the retrograde movement of fluids during the use of air eliminating filters in intravenous therapy by preventing the displacement of air into the proximal chamber of an air eliminating filter.

BRIEF DESCRIPTION OF THE DRAWINGS

The foregoing summary, as well as the following detailed description of a preferred embodiment of the invention, will be better understood when read in conjunction with the appended drawings. For purposes of illustrating the invention, there is shown in the drawings an embodiment which is presently preferred. It should be understood, however, that the invention is not limited to the precise arrangement and instrumentality shown. In the drawings.

DETAILED DESCRIPTION OF THE INVENTION

Figure 1:
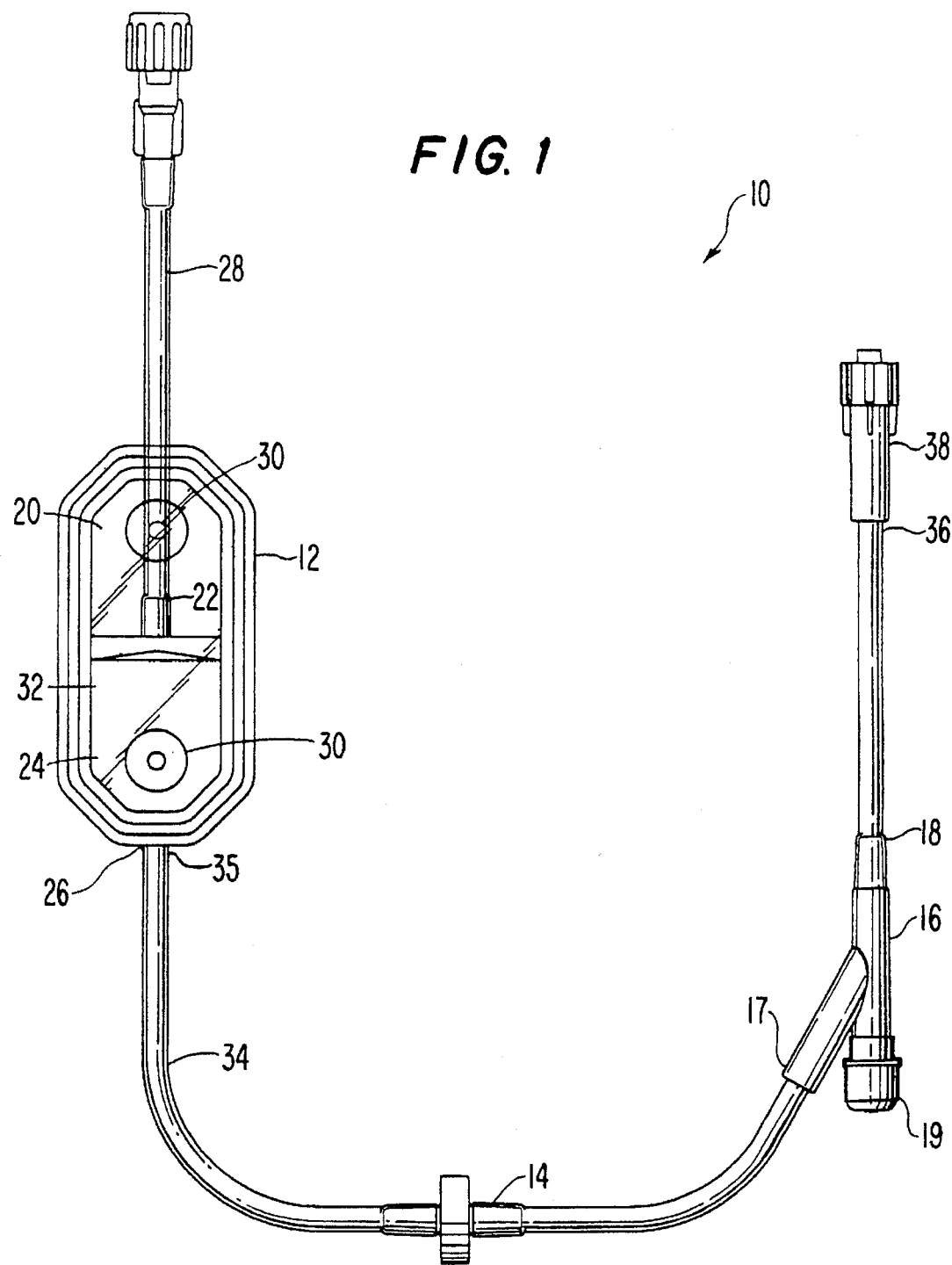
FIG. 1 is an environmental view of a portion of an intravenous fluid delivery system in accordance with one embodiment of the present invention.

Referring now to the drawings, wherein similar reference characters designate corresponding parts throughout the several views, an intravenous fluid delivery system in accordance with the teachings of the present invention is illustrated generally at 10 in FIG. 1. As illustrated therein, the intravenous fluid delivery system 10 comprises an air eliminating filter 12 (AEF), a fluid valve assembly 14 (e.g., a check valve), and a fluid injection port 16, which in the illustrated embodiment is a "Y" site fluid injection port.

Typically, the AEF 12 is located approximately twelve inches from an infusion site of a patient (not shown) who is receiving intravenous therapy. The AEF 12 comprises a proximal AEF chamber 20, a proximal AEF fluid inlet 22, a distal AEF chamber 24 and a distal AEF fluid outlet 26. The proximal AEF fluid inlet 22 is fluidly connected to the proximal AEF chamber 20. A length of polymeric tubing 28 fluidly connects a source of intravenous fluid (not shown) to the proximal AEF chamber 20, through the proximal AEF inlet 22. At least one vent port 30 may be provided at the proximal AEF chamber 20. Attached at the vent port 30 is a vent material (not shown) which may be defined by a suitable hydrophobic microporous membrane, such as but not limited to, a porous fluoropolymer material such as porous polytetrafluoroethylene (PTFE), or any other suitable material such as polyvinyl difluoride (PVDF), or polypropylene.

The proximal AEF chamber 20 is separated from the distal AEF chamber 24 by a liquid filter element or filtration media 32. The filtration media 32 may be defined by a suitable hydrophilic microporous membrane, such as but not limited to, polyethersulfone (PES), cellulose acetate, polysulfone, or nylon. The distal AEF chamber 24 is fluidly connected to the distal AEF fluid outlet 26. At least one vent port 30, and a vent material (not shown), may also be provided at the distal AEF chamber 24. Fluidly connected to the distal AEF chamber 24, by way of the distal AEF fluid outlet 26, is a length of fluid conveying intravenous tubing 34, such as but not limited to a polymeric tubing. The length of fluid conveying tubing defines opposed first and second ends, 35, 36, respectively. The first tubing end 35 is fluidly connected to the distal AEF chamber 24 at the distal AEF fluid outlet 26. Disposed at the second or distal end 36 of the tubing 34 is a suitable fluid connector 38 which permits the distal end 36 to be securely fluidly connected to an infusion site of a patient or an infusion catheter (both not shown). One type fluid connector 38 may be a LUER-LOK® type fluid connector which may be obtained by the Becton Dickinson Company. (LUER-LOK is a registered trademark of the Becton Dickinson Company). A suitable AEF 12 may be obtained from Gelman Sciences Inc. of Ann Arbor, Mich., or from Millipore Corporation of Bedford, Massachusetts.

As illustrated in FIG. 1, the "Y" site fluid injection port 16 is located between the AEF 12 and the infusion site of the patient. The "Y" site fluid injection port 16 includes an inlet portion 17, an outlet portion 18, and an injection site portion 19. Prescribed intravenous fluid flowing from the distal AEF chamber 24 arrives at the inlet portion 17 of the "Y" site injection port 16 by way of the tubing 34. The "Y" site injection port 16 permits fluids, which are either deemed too critical to be filtered, or which are not compatible with an AEF, to be introduced into the intravenous fluid delivery system 10. Although the exact location of the "Y" site injection port 16 may vary, typically, a preferred location is at a mid-point location between the AEF 12 and the distal end 36 of the polymeric tubing 34.

As is well known, the introduction or displacement of air into the proximal AEF chamber 20 may cause retrograde movement of prescribed intravenous fluids away from a patient, thereby causing detrimental clinical situations to arise. Typically, air is introduced into the proximal AEF chamber when the AEF 12 is disposed in a position higher than the infusion site. In one embodiment of the present invention, it has been discovered that retrograde movement of prescribed intravenous fluids is prevented by operation of the fluid valve assembly or check valve 14, which is positioned between the proximal AEF chamber 20 and the distal end 36 of the polymeric tubing 34. In a preferred embodiment of the present invention, the fluid valve assembly or check valve 14 is positioned between the distal AEF fluid outlet 26 and the distal end 36 of the polymeric tubing 34.

Optimally, the fluid check valve 14 is located approximately two inches from the distal AEF fluid outlet 26. In this location, the fluid check valve 14 will prevent retrograde movement of prescribed intravenous fluids administered at low infusion rates; prevent retrograde movement of prescribed intravenous fluids caused by an empty proximal AEF chamber 20; and prevent retrograde movement of prescribed intravenous fluids that have been injected distally to the AEF 12, at either a fluid injection port, a "Y" site injection port, or an injection port collar located at the distal end 36 of the tubing 34.

As should be understood, the injection port 16 may be fluidly connected with the tubing 34 at a location between the check valve 14 and the distal AEF fluid outlet 26, or at a location between the check valve 14 and the distal end 36 of the tubing 34. In a preferred embodiment of the present invention, the fluid injection port 16 is fluidly connected with the tubing 34 at a location between the check valve 14 and the distal end 36 of the tubing 34.

Any suitable valve assembly 14, which permits a flow of prescribed fluid from the distal fluid outlet of the air eliminating filter to the infusion site of the patient, and which prevents a retrograde flow of prescribed fluid away from the patient, may be employed. For example, "wafer" or "flapper" type and "duckbill" type fluid valves may be employed in the intravenous delivery system 10. Such valves operate by permitting a desired intravenous fluid to pass through toward a patient, however, if a retrograde movement of fluids begins to occur, the fluid valve closes. The fluid valve assembly 14 remains closed until the retrograde fluid movement ceases, or until the pressure of the fluid stream is greater than the retrograde pressure. Other suitable types of fluid valve assemblies include, but are not limited to, a "ball" type check valve. Suitable fluid valve assemblies may be obtained from B. Braun Medical Inc. of Bethlehem, Penn. or Medex Inc. of Hilliard, Ohio.

Figure 4:
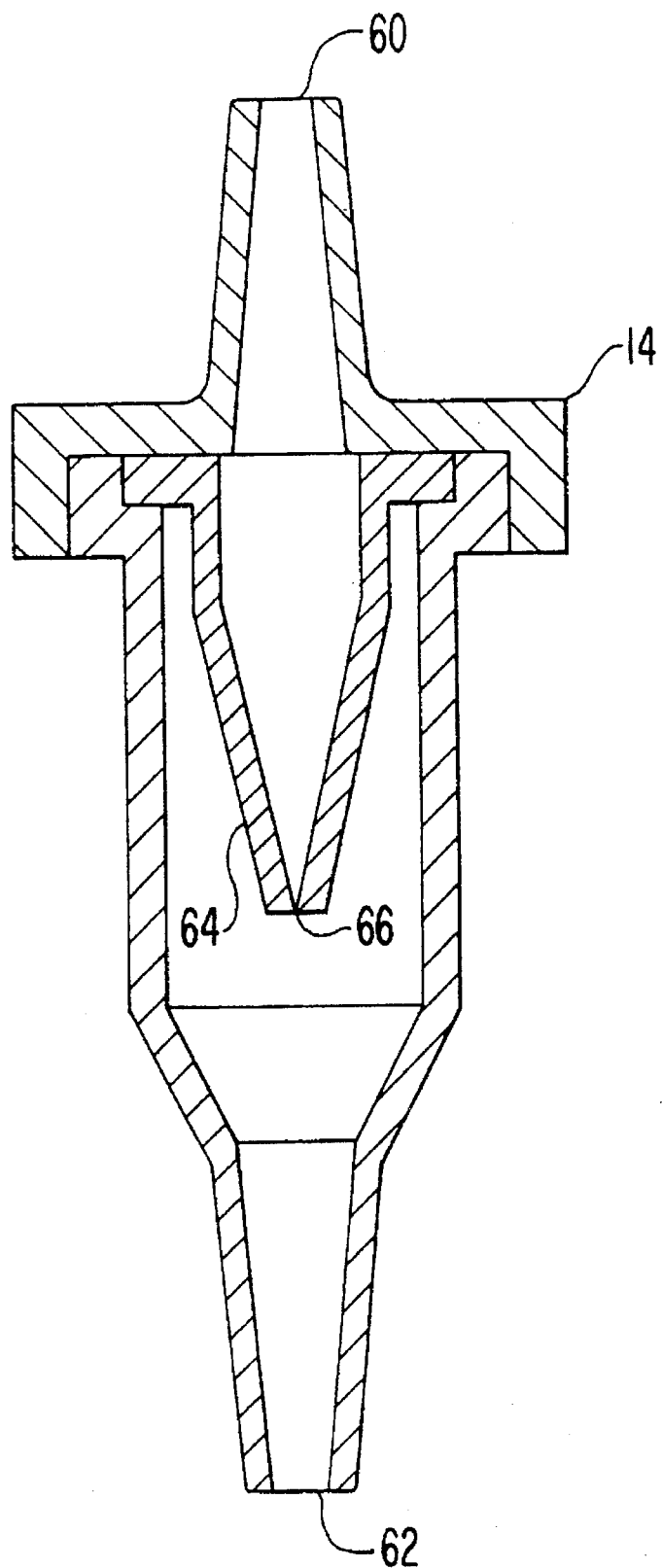
FIG. 4 is a side sectional view of a fluid valve assembly for use in accordance with the teachings of the present invention.

A suitable valve assembly 14 is best understood by reference to FIG. 4 illustrated therein is a "duckbill" type check valve having a fluid inlet 60 and a fluid outlet 62. The valve itself is a conical wedge shaped member 64 which defines an interior fluid passageway. A slit 66, normally closed, is defined at an outlet of the conical wedge shaped member. The slit remains in a closed position until a fluid entering the valve with sufficient force (approximately 0.1 pounds per square inch) causes the slit to open and to allow the fluid to pass therethrough. Fluid attempting to enter the valve 14 in a retrograde fashion, i.e. through the fluid outlet, will cause the slit to close, thereby preventing retrograde movement of fluid from the patient.

In addition to preventing retrograde movement of fluids during intravenous therapy by the employment of a fluid valve 14, as described hereinabove, it has additionally been discovered that such retrograde movement of fluids may be prevented by providing an improved AEF 12 comprising at least one novel vented valve assembly which restricts the entry of air into internal portions of the AEF. Such an improved AEF 12 is described in further detail hereinafter. As should be understood, the novel vented valve assembly of the present invention may be either external, or internal, to the improved AEF 12.

Figure 2:
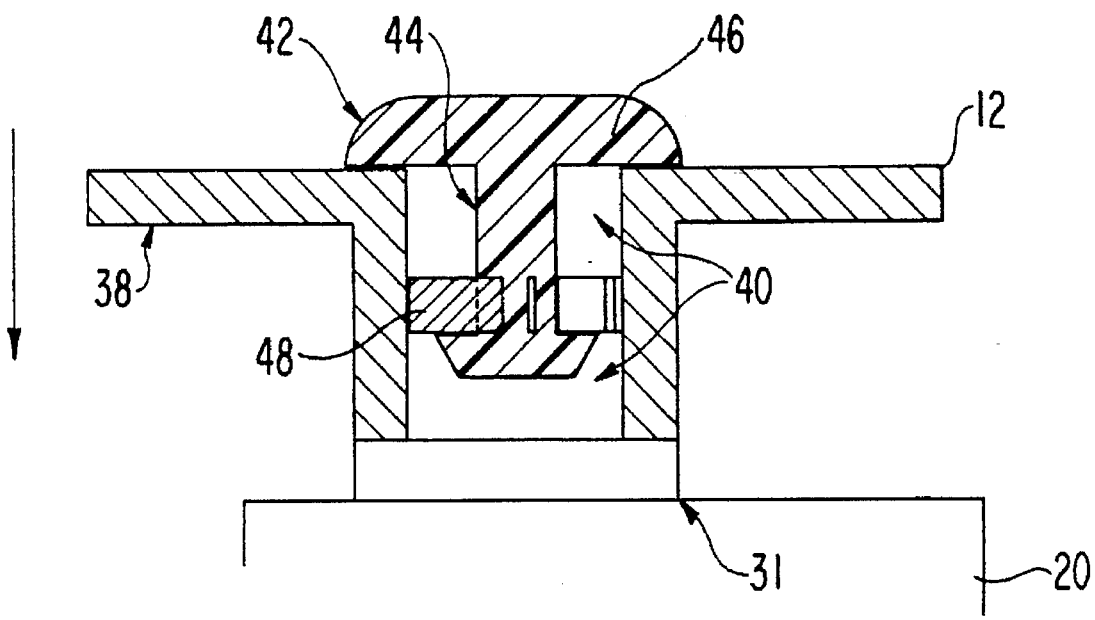
FIG. 2 is a side sectional view of an external air eliminating filter vented valve assembly in accordance with the teachings of the present invention.

FIG. 2 is a side sectional view of one embodiment of an external vented valve assembly in accordance with the teachings of the present invention. As illustrated therein, an external valve, generally illustrated at 42, such as but not limited to a mushroom or umbrella type valve for example, is incorporated into an AEF housing. The external vented valve 42 permits air or gases to be continuously vented from the proximal AEF chamber 20, to an atmosphere external to the proximal AEF chamber, during use of the AEF 12, but will not allow air or gases to enter back into the proximal AEF chamber from the external atmosphere. In operation, the external valve 42 seals over the vent port 30 by negative pressure formed when fluid attempts to flow out of the proximal AEF chamber 20 into the distal AEF chamber 24.

The incorporation of an external vented valve 42 into the AEF 12 may be accomplished, for example, by forming a vent port well 40 within the AEF 12. The vented valve assembly 42 is inserted within the vent port well 40.

As illustrated in FIG. 2, one possible external vented valve assembly is a mushroom valve 42 which is comprised of a valve stem 44 and a sealing member 46. The sealing member 46 is circular shaped having a suitably dimensioned diameter to sealingly cover the vent port 30 and vent material (not shown) of the AEF 12. The sealing member 46 must be sufficiently pliable to be drawn down and seal the vent port 30 with minimal negative pressure of about 0.1 pounds per square inch. Suitable materials for the sealing member 46 include, but are not limited to polyvinyl chloride (PVC), latex materials or silicone materials. The sealing member 46 must also remain in an open position with minimal positive pressure (about 0.1 pounds per square inch) during active air venting of the proximal AEF chamber 20. The valve stem 44 may be comprised of the same material as the sealing member 46. The valve stem 44 should be of sufficient length to be inserted into the vent port well 40 to slidably secure the external vented valve 42 with a stop member 48. During operation of the external valve 42, the valve stem 44 and the sealing member 46 travel, back and forth, along a path of travel "A" to selectively seal the vent port 30. Sufficient clearance, e.g., about 1/1000 inches, between an external surface of the AEF 12 and the sealing member 46 exists to facilitate normal venting of the proximal AEF chamber 20.

Figure 3:
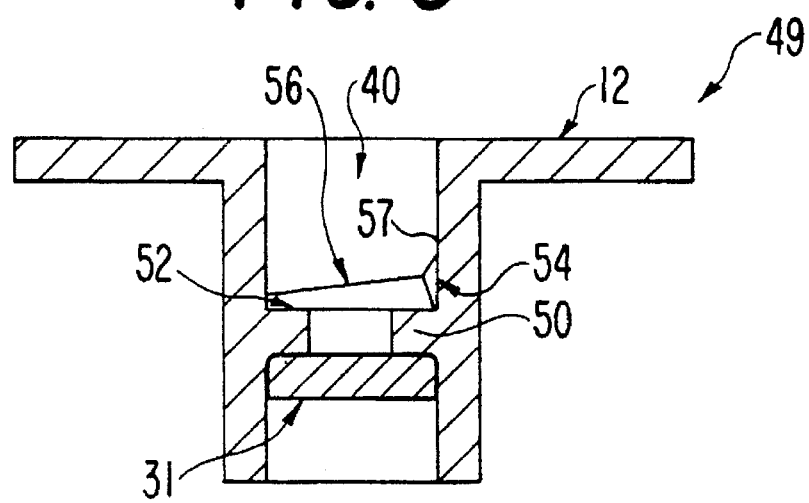
FIG. 3 is a side sectional view of an internal air eliminating filter vented valve assembly in accordance with the teachings of the present invention.

Alternatively, and as best illustrated in FIG. 3, an internal vented valve assembly 49 may be incorporated within the body of the AEF 12. Such a valve comprises a valve member which is movably attached to a side wall portion of the vent port well 40. More particularly, the valve member 56 is attached to a side wall portion 57 by an attaching member 54. A shoulder portion 50 is formed in the vent port well 40. Shoulder portion 50 is suitably dimensioned to form a seal with the valve member 56. As with the external vented valve 42, the internal valve will close when acted upon by negative pressure caused by fluid attempting to leave the proximal AEF chamber 20. Because fluid is prevented from emptying from the proximal AEF chamber 20, retrograde movement of fluid is prevented.

As should be understood, the external vented valve 42 and the internal vented valve 49 must be located between the vent material (not shown) and the environment external to the proximal AEF chamber 20. Also, the number of vented valves 42 employed must be at least equal to the number of vent ports 30.

Although a few exemplary embodiments of the present invention have been described in detail above, those skilled in the art readily appreciate that many modifications are possible without materially departing from the novel teachings and advantages which are described herein. Accordingly, all such modifications are intended to be included within the scope of the present invention, as defined by the following claims.

Having described the invention, what is claimed is:

1. An improved air eliminating filter in combination with an intravenous fluid line for use in intravenous therapy, the air eliminating filter having a proximal fluid chamber disposed in fluid communication with a proximal fluid inlet, and a distal fluid chamber disposed in fluid communication with a distal fluid outlet, said proximal fluid chamber and said distal fluid chamber being fluidly connected through a liquid filter element, the improvement comprising:

a one-way vented valve assembly for venting the proximal fluid chamber, said one-way vented valve assembly permitting gases to vent from the proximal fluid chamber to an atmosphere external to the proximal fluid chamber, and restricting a flow of gases from the external atmosphere into the proximal fluid chamber.

2. An improved air eliminating filter in combination with an intravenous fluid line for use in intravenous therapy, the air eliminating filter having a proximal fluid chamber disposed in fluid communication with a proximal fluid inlet, and a distal fluid chamber disposed in fluid communication with a distal fluid outlet, said proximal fluid chamber and said distal fluid chamber being fluidly connected through a liquid filter element, the improvement comprising:

a one-way valve for venting the proximal fluid chamber to an external atmosphere.

* * * * *